United States Patent
Devoe et al.

(10) Patent No.: US 9,023,555 B2
(45) Date of Patent: May 5, 2015

(54) METHOD OF MAKING A FUEL CELL DEVICE

(71) Applicants: Alan Devoe, La Jolla, CA (US); Lambert Devoe, San Diego, CA (US)

(72) Inventors: Alan Devoe, La Jolla, CA (US); Lambert Devoe, San Diego, CA (US)

(*) Notice: Subject to any disclaimer, the term of this patent is extended or adjusted under 35 U.S.C. 154(b) by 101 days.

(21) Appl. No.: 13/773,044

(22) Filed: Feb. 21, 2013

(65) Prior Publication Data
US 2013/0273462 A1    Oct. 17, 2013

Related U.S. Application Data

(60) Provisional application No. 61/623,814, filed on Apr. 13, 2012.

(51) Int. Cl.
| | | |
|---|---|---|
| H01M 4/02 | (2006.01) | |
| G01N 27/416 | (2006.01) | |
| H01M 8/10 | (2006.01) | |
| G01N 27/08 | (2006.01) | |
| H01M 8/02 | (2006.01) | |

(52) U.S. Cl.
CPC ............. *G01N 27/4166* (2013.01); *H01M 8/10* (2013.01); *G01N 27/08* (2013.01); *H01M 8/0258* (2013.01); *H01M 8/026* (2013.01)

(58) Field of Classification Search
CPC ..... G01N 27/08; G01N 27/4166; H01M 8/10; H01M 8/0258; H01M 8/026; H01M 8/258; H01M 10/5057; H01M 2008/10
USPC ......... 429/407, 456, 457, 458, 465, 479, 513, 429/523, 535
See application file for complete search history.

(56) References Cited

U.S. PATENT DOCUMENTS

| | | |
|---|---|---|
| 3,120,456 A | 2/1964 | Broers |
| 4,395,468 A | 7/1983 | Isenberg |

(Continued)

FOREIGN PATENT DOCUMENTS

| | | |
|---|---|---|
| DE | 10117985 | 10/2002 |
| EP | 0321069 | 6/1989 |

(Continued)

OTHER PUBLICATIONS

European Patent Office, International Search Report and Written Opinion issued in corresponding Application No. PCT/US2013/027304, Jan. 3, 2014, 10 pp.

(Continued)

*Primary Examiner* — Patrick Ryan
*Assistant Examiner* — Ben Lewis
(74) *Attorney, Agent, or Firm* — Wood, Herron & Evans, LLP

(57) ABSTRACT

A monolithic fuel cell device is provided by forming anode and cathode layers by dispensing paste of anode or cathode material around pluralities of spaced-apart removable physical structures to at least partially surround the structures with the anode or cathode material and then drying the paste. An electrolyte layer is provided in a multi-layer stack between the cathode layer and the anode layer thereby forming an active cell portion. The multi-layer stack is laminated, and then the physical structures are pulled out to reveal spaced-apart active passages formed through each of the anode layer and cathode layer. Finally, the laminated stack is sintered to form an active cell comprising the spaced apart active passages embedded in and supported by the sintered anode material and sintered cathode material.

16 Claims, 8 Drawing Sheets

(56) References Cited

U.S. PATENT DOCUMENTS

| | | | |
|---|---|---|---|
| 4,413,041 A | 11/1983 | Hegedus | |
| 4,414,337 A | 11/1983 | Ichikawa et al. | |
| 4,463,687 A | 8/1984 | Zimmerman et al. | |
| 4,490,444 A | 12/1984 | Isenberg | |
| 4,591,470 A | 5/1986 | Goto et al. | |
| 4,808,491 A | 2/1989 | Reichner | |
| 4,913,982 A | 4/1990 | Kotchick et al. | |
| 4,943,494 A | 7/1990 | Riley | |
| 5,034,288 A | 7/1991 | Bossel | |
| 5,185,219 A | 2/1993 | Ishihara et al. | |
| 5,317,805 A | 6/1994 | Hoopman et al. | |
| 5,356,728 A | 10/1994 | Balachandran et al. | |
| 5,380,601 A | 1/1995 | Jaspers et al. | |
| 5,770,326 A | 6/1998 | Limaye | |
| 5,864,743 A | 1/1999 | Tuchinskiy et al. | |
| 6,007,932 A | 12/1999 | Steyn | |
| 6,291,089 B1 | 9/2001 | Piascik et al. | |
| 6,444,339 B1 | 9/2002 | Eshraghi | |
| 6,458,477 B1 | 10/2002 | Hsu | |
| 6,767,662 B2 | 7/2004 | Jacobson et al. | |
| 6,841,284 B2 | 1/2005 | Brown et al. | |
| 6,846,511 B2 | 1/2005 | Visco et al. | |
| 6,949,307 B2 | 9/2005 | Cable et al. | |
| 7,838,137 B2 | 11/2010 | Devoe et al. | |
| 7,842,429 B2 | 11/2010 | Devoe et al. | |
| 7,883,816 B2 | 2/2011 | Devoe et al. | |
| 7,981,565 B2 | 7/2011 | Devoe et al. | |
| 7,989,113 B2 | 8/2011 | Matsuzaki et al. | |
| 8,029,937 B2 | 10/2011 | Devoe et al. | |
| 8,153,318 B2 | 4/2012 | Devoe et al. | |
| 8,227,128 B2 | 7/2012 | Devoe et al. | |
| 8,257,884 B2 | 9/2012 | Devoe et al. | |
| 8,278,013 B2 | 10/2012 | Devoe et al. | |
| 8,293,415 B2 | 10/2012 | Devoe et al. | |
| 8,293,417 B2 | 10/2012 | Devoe et al. | |
| 8,293,429 B2 | 10/2012 | Devoe et al. | |
| 8,309,266 B2 | 11/2012 | Devoe et al. | |
| 8,343,684 B2 | 1/2013 | Devoe et al. | |
| 2001/0044043 A1 | 11/2001 | Badding et al. | |
| 2002/0018924 A1 | 2/2002 | Saito et al. | |
| 2002/0102450 A1 | 8/2002 | Badding et al. | |
| 2002/0146523 A1 | 10/2002 | Devoe et al. | |
| 2002/0146611 A1 | 10/2002 | Kawasaki et al. | |
| 2002/0197520 A1 | 12/2002 | Quick et al. | |
| 2003/0013046 A1 | 1/2003 | Fonash et al. | |
| 2003/0235745 A1 | 12/2003 | Mook et al. | |
| 2004/0020781 A1 | 2/2004 | Dordi et al. | |
| 2004/0020782 A1 | 2/2004 | Cohen et al. | |
| 2004/0067404 A1 | 4/2004 | Lazaroff et al. | |
| 2004/0081878 A1 | 4/2004 | Mardilovich et al. | |
| 2004/0086767 A1 | 5/2004 | Lazaroff et al. | |
| 2004/0110054 A1 | 6/2004 | Bourgeois et al. | |
| 2004/0183055 A1 | 9/2004 | Chartier et al. | |
| 2004/0185318 A1 | 9/2004 | Novak | |
| 2004/0185321 A1 | 9/2004 | Sutherland et al. | |
| 2004/0247972 A1 | 12/2004 | Kendall et al. | |
| 2004/0258972 A1 | 12/2004 | Du et al. | |
| 2005/0000621 A1 | 1/2005 | Devoe et al. | |
| 2005/0116190 A1 | 6/2005 | Adams et al. | |
| 2005/0208363 A1 | 9/2005 | Taylor et al. | |
| 2006/0003213 A1 | 1/2006 | Ketcham et al. | |
| 2006/0008696 A1* | 1/2006 | Cha et al. | 429/38 |
| 2006/0035130 A1 | 2/2006 | Noda et al. | |
| 2006/0175194 A1 | 8/2006 | Bagby et al. | |
| 2007/0104991 A1 | 5/2007 | Devoe et al. | |
| 2007/0105003 A1 | 5/2007 | Devoe et al. | |
| 2007/0243445 A1 | 10/2007 | Digiuseppe | |
| 2007/0264542 A1 | 11/2007 | Devoe et al. | |
| 2008/0233462 A1 | 9/2008 | Curello et al. | |
| 2008/0289180 A1 | 11/2008 | Brantley et al. | |
| 2009/0226781 A1 | 9/2009 | Devoe et al. | |
| 2010/0104910 A1 | 4/2010 | Devoe et al. | |
| 2011/0117471 A1* | 5/2011 | Devoe et al. | 429/457 |
| 2011/0200910 A1 | 8/2011 | Wachsman et al. | |

FOREIGN PATENT DOCUMENTS

| | | |
|---|---|---|
| EP | 0387643 | 9/1990 |
| EP | 0442742 | 8/1991 |
| EP | 0756347 | 1/1997 |
| EP | 1333519 | 8/2003 |
| EP | 1445817 | 8/2004 |
| EP | 1447871 A1 | 8/2004 |
| EP | 1612876 | 1/2006 |
| EP | 1650821 | 4/2006 |
| FR | 2877496 | 5/2006 |
| JP | 01320778 | 12/1989 |
| JP | 02075167 | 3/1990 |
| JP | 08050914 | 2/1996 |
| JP | 08106908 | 4/1996 |
| JP | 10189017 | 7/1998 |
| JP | 2000164239 | 6/2000 |
| JP | 2002151100 A | 5/2002 |
| JP | 2002151101 A | 5/2002 |
| JP | 2002184429 A | 6/2002 |
| JP | 2004030972 | 1/2004 |
| JP | 2004134323 | 4/2004 |
| JP | 2004152645 | 5/2004 |
| WO | 9422178 | 9/1994 |
| WO | 0124300 A1 | 4/2001 |
| WO | 0225763 | 3/2002 |
| WO | 03001624 | 1/2003 |
| WO | 03005462 | 1/2003 |
| WO | 03036746 | 5/2003 |
| WO | 03/081703 A2 | 10/2003 |
| WO | 03096469 | 11/2003 |
| WO | 2004082050 | 9/2004 |
| WO | 2006048573 | 5/2006 |
| WO | 2007005767 | 1/2007 |
| WO | 2007056518 | 5/2007 |
| WO | 2007134209 | 11/2007 |
| WO | 2008141171 A2 | 11/2008 |
| WO | 2009062127 | 5/2009 |
| WO | 2009111771 A1 | 9/2009 |

OTHER PUBLICATIONS

NGK Insulators, Ltd., Translation of Japanese Patent Application Publication JP2002-151100, 7 pp.

NGK Insulators, Ltd., Translation of Japanese Patent Application Publication JP2002-151101, 10 pp.

Japanese Patent Office, Office Action issued in related JP Patent Application No. 2008-540191dated Mar. 19, 2013, 6 pp. (English translation of Rejections).

Japanese Patent Office, Office Action issued in related JP Patent Application No. 2009-510182 dated Mar. 19, 2013, 7 pp. (English translation of Rejections).

Fuel Cell Energy, Timeline, www.fce.com/site/products/sofc/timeline1.html and www.fce.com/site/products/sofc/timeline2.html, 4 pp, Aug. 28, 2009.

Fuelcell Energy, Inc. et al., Thermally Integrated High Power Density SOFC Generator, SECA Annual Meeting, Pacific Grove, CA, Apr. 18-21, 2005, 42 pp., Distributed Energy Corporation.

Vora, S.D., SECA Program at Siemens Westinghouse, Sixth Annual SECA Workshop, Pacific Grove, CA, Apr. 18, 2005, 44 pp., Siemens Westinghouse Power Corporation.

Acumentrics Corporation, How Acumentrics Fuel Cells Work, 2004, 12 pp.

Vora, Shailesh D., Small-Scale Low-Cost Solid Oxide Fuel Cell Power Systems, Office of Fossil Energy Fuel Cell Program, FY 2004 Annual Report, pp. 33-35.

Zurich University of Applied Sciences, Hexis Co-Generation System, Nov. 8-9, 2004, 2 pp., Berlin.

Subhash C. Singhal et al., High Temperature Solid Oxide Fuel Cells: Fundamentals, Design and Applications, Chapter 1, Introduction to SOFCs, 2003, pp. 1-22.

Subhash C. Singhal et al., High Temperature Solid Oxide Fuel Cells: Fundamentals, Design and Applications, Chapter 2, History, 2003, pp. 23-51.

Subhash C. Singhal et al., High Temperature Solid Oxide Fuel Cells: Fundamentals, Design and Applications, Chapter 8, Cell and Stack Designs, 2003, pp. 197-228.

(56) References Cited

OTHER PUBLICATIONS

Siemens, Siemens Power Generation: Next Generation SOFC, www.powergeneration.siemens.com/en/fuelcells/seca/index.cfm?session=1142501x39517655, 2 pp. <http://www.powergeneration.siemens.com/en/fuelcells/seca/index.cfm?session=1142501x39517655>, 2007.

SOFCo-EFS Fuel Cell and Fuel Processor Solutions, Solid Oxide Fuel Cell Technology and SOFCo-EFS, www.sofco-efs.com/technology/sofctech/, 2 pp. <http://www.sofco-efs.com/technology/sofctech/>, Aug. 28, 2005.

Ben Wiens Energy Science, Solid Oxide Fuel Cell (SOFC), The Future of Fuel Cells, www.benwiens.com/energy4.html, 2 pp. <http://www.benwiens.com/energy4.html>, Aug. 28, 2005.

Ceramic Fuel Cells Limited, CFCLs Stack Design, www.cfcl.com.au/html/p_stack_design.htm, 3 pp. <http://www.cfcl.com.au/html/p_stack_design.htm>, Aug. 28, 2005.

Miwa, Taiichiro et al., Japan-Finland Cooperation in Technological Research & Development: R&D Status of Fuel Cell in Japan, Jun. 15, 2005, 19 pp., DIA Research Martech Inc., Espoo, Finland.

Norrick, Dan, 10kWe SOFC Power System Commercialization Program Progress, SECA Annual Workshop, Pacific Grove, CA, Apr. 20, 2005, 67 pp., Cummins Power Generation.

Shaffer, Steven, Development Update on Delphi's Solid Oxide Fuel Cell System, 2005 SECA Review Meeting, Pacific Grove, CA, Apr. 20, 2005, 41 pp., Delphi.

GE Hybrid Power Generation Systems, SECA Solid Oxide Fuel Cell Program, Sixth SECA Annual Workshop, Pacific Grove, CA, Apr. 18-21, 2005, 28 pp., GE Energy.

Tokyo Gas Co., Ltd, Environmental Affairs Dept, Environmental Report 2004, Environmental Technology Development, Measures Taken Within the Tokyo Gas Group, pp. 28-29, Tokyo, Japan.

Bessette, Norman, Status of the Acumentrics SOFC Program, SEC Annual Workshop, Boston, MA, May 11, 2004, 47 pp., Acumentrics Corporation.

Kyocera Corporation, 1kW Solid Oxide Fuel Cell (SOFC) for Small-Scale Power Generation: Worlds Highest Efficiency for 1kW Class Power Generation, News Release, http://global.kyocera.com/news/2003/1205.html, Dec. 18, 2003, 4 pp. <http://global.kyocera.com/news/2003/1205.html>.

Talbot, David, Flying the Efficient Skies, Technology Review, www.technologyreview.com/articles/03/06innovation80603.0.asp, Jun. 2003, 1 pp.

De Guire, Eileen J., Solid Oxide Fuel Cells, Internet article, www.csa.com/hottopics/fuecel/overview.php, CSA Illumina, Apr. 2003, 8 pp. <http://www.csa.com/hottopics/fuecel/overview.php>.

Lawrence Livermore National Laboratory, Solid-Oxide Fuel Cells Stack Up to Efficient, Clean Power, S&TR, Research Highlights, Sep. 2002, 3 pp.

Nissan Motor Co Ltd, English translation of Patent Abstract of Japan Publication No. 2004-134323 entitled Solid Oxide Fuel Cell, published Apri. 30, 2004, 2 pp.

* cited by examiner

METHOD OF MAKING A FUEL CELL DEVICE

CROSS REFERENCE TO RELATED APPLICATION

Pursuant to 37 C.F.R. §1.78(a)(4), this application claims the benefit of and priority to prior filed Provisional Application Ser. No. 61/632,814 filed Feb. 24, 2012, which is expressly incorporated herein by reference.

FIELD OF THE INVENTION

This invention relates to fuel cell devices and systems, and methods of manufacturing the devices, and more particularly, to a solid oxide fuel cell device.

BACKGROUND OF THE INVENTION

Ceramic tubes have found a use in the manufacture of Solid Oxide Fuel Cells (SOFCs). There are several types of fuel cells, each offering a different mechanism of converting fuel and air to produce electricity without combustion. In SOFCs, the barrier layer (the "electrolyte") between the fuel and the air is a ceramic layer, which allows oxygen atoms to migrate through the layer to complete a chemical reaction. Because ceramic is a poor conductor of oxygen atoms at room temperature, the fuel cell is operated at 700° C. to 1000° C., and the ceramic layer is made as thin as possible.

Early tubular SOFCs were produced by the Westinghouse Corporation using long, fairly large diameter, extruded tubes of zirconia ceramic. Typical tube lengths were several feet long, with tube diameters ranging from ¼ inch to ½ inch. A complete structure for a fuel cell typically contained roughly ten tubes. Over time, researchers and industry groups settled on a formula for the zirconia ceramic which contains 8 mol % $Y_2O_3$. This material is made by, among others, Tosoh of Japan as product TZ-8Y.

Another method of making SOFCs makes use of flat plates of zirconia, stacked together with other anodes and cathodes, to achieve the fuel cell structure. Compared to the tall, narrow devices envisioned by Westinghouse, these flat plate structures can be cube shaped, 6 to 8 inches on an edge, with a clamping mechanism to hold the entire stack together.

A still newer method envisions using larger quantities of small diameter tubes having very thin walls. The use of thin walled ceramic is important in SOFCs because the transfer rate of oxygen ions is limited by distance and temperature. If a thinner layer of zirconia is used, the final device can be operated at a lower temperature while maintaining the same efficiency. Literature describes the need to make ceramic tubes at 150 μm or less wall thickness.

An SOFC tube is useful as a gas container only. To work it must be used inside a larger air container. This is bulky. A key challenge of using tubes is that you must apply both heat and air to the outside of the tube; air to provide the $O_2$ for the reaction, and heat to accelerate the reaction. Usually, the heat would be applied by burning fuel, so instead of applying air with 20% $O_2$ (typical), the air is actually partially reduced (partially burned to provide the heat) and this lowers the driving potential of the cell.

An SOFC tube is also limited in its scalability. To achieve greater kV output, more tubes must be added. Each tube is a single electrolyte layer, such that increases are bulky. The solid electrolyte tube technology is further limited in terms of achievable electrolyte thinness. A thinner electrolyte is more efficient. Electrolyte thickness of 2 μm or even 1 μm would be optimal for high power, but is very difficult to achieve in solid electrolyte tubes. It is noted that a single fuel cell area produces about 0.5 to 1 volt (this is inherent due to the driving force of the chemical reaction, in the same way that a battery gives off 1.2 volts), but the current, and therefore the power, depend on several factors. Higher current will result from factors that make more oxygen ions migrate across the electrolyte in a given time. These factors are higher temperature, thinner electrolyte, and larger area.

Fuel utilization is a component of the overall efficiency of the fuel cell. Fuel utilization is a term that can describe the percent of fuel that is converted into electricity. For example, a fuel cell may only convert 50% of its fuel into electricity, with the other 50% exiting the cell un-used. Ideally, the fuel utilization of a fuel cell would be 100%, so that no fuel is wasted. Practically, however, total efficiency would be less than 100%, even if fuel utilization was 100%, because of various other inefficiencies and system losses. Additionally, if the gas molecules can't get into and out of the anode and cathode, then the fuel cell will not achieve its maximum power. A lack of fuel or oxygen at the anodes or cathodes essentially means that the fuel cell is starved for chemical energy. If the anode and/or cathode are starved for chemicals, less power will be generated per unit area ($cm^2$). This lower power per unit area gives lower total system power.

In a tubular fuel cell device, such as that shown in FIG. 1 where the anode lines the inside of the tube and the cathode forms the outer surface with the electrolyte therebetween, it is wishful thinking to expect high utilization of fuel. The inside diameter of the tube, which forms the fuel passage, is very large when compared to the thickness of the anode. Anode thicknesses may be on the order of 50-500 nm, whereas tube diameters may be on the order of 4-20 mm. Thus, there is a high likelihood of fuel molecules passing through the large fuel passage without ever entering the pores of the anode. An alternate geometry for the tube is to have the anode on the outside of the tube. In that case, the problem could be worse because the fuel is contained within the furnace volume, which is even larger than the volume within the tube.

Within a multilayer fuel cell device, such as the Fuel Cell Stick™ devices 10 depicted in FIGS. 2 and 3 and developed by the present inventors, fuel utilization can be higher because the flow path for the gas can be smaller. FIG. 2 is identical to FIG. 1 of U.S. Pat. No. 7,838,137, the description of which is incorporated by reference herein. Device 10 includes a fuel inlet 12 feeding a fuel passage 14 to a fuel outlet 16, and an oxidizer inlet 18 feeding an oxidizer passage 20 to an oxidizer outlet 22. An anode 24 is adjacent the fuel passage 14 and a cathode 26 is adjacent the oxidizer passage 20, with an electrolyte 28 therebetween. By way of example, both the anodes 24 and fuel passages 14 can be made to a thickness of 50 nm, and this similarity in thickness, where the ratio of thickness can be near 1:1 (or a bit higher or lower, such as 2:1 or 1:2) can give a more optimal chance of molecule flow into and out of pores.

These multilayer fuel devices 10 are built from green materials, layer by layer, and then laminated and co-fired (sintered) to form a single monolithic device having a ceramic support structure 29 surrounding one or more active cells 50, each active cell 50 having an associated anode 24, cathode 26 and electrolyte 28 fed by fuel and air passages 14, 20. An active cell 50 (or active layer 50) is one in which an anode 24 is in opposing relation to a cathode 26 with an electrolyte 28 therebetween, and the active passages are those that run along or within the active cell 50. FIG. 3 depicts two active cells 50. Areas of the device 10 that lack an opposed anode 24 and cathode 26 are non-active or passive portions of the device 10 that form the support structure 29, and passive gas passages are those that run through these passive portions of the device 10. The active cells 50 are "within" the device 10 and substantially surrounded by and supported by ceramic support structure 29. The device has an exterior surface and internal supporting structure, which is the ceramic support structure 29, such that the active cells 50 are contained substantially inward of the exterior surface and are contained by the internal ceramic support structure. It should be understood that extension of all or a portion of an electrode to an edge of the device for electrical connection at the exterior surface does not compromise the support of this structure as the active cell 50 is still within the interior structure, and is within the scope of "substantially surrounded." The electrolyte 28 in the active cell 50 is monolithic with the ceramic support structure 29 by virtue of being co-fired therewith, and may be made of the same or different material. In exemplary embodiments, the electrolyte 28 and ceramic support structure 29 are the same or similar in composition, with the primary difference between them being that the electrolyte 28 is that portion of the ceramic material that lies between an opposing anode 24 and cathode 26 (i.e., the middle layer in the 3-layer active cell 50) and the ceramic support structure 29 is the remaining portion of the ceramic material (i.e., the ceramic that surrounds the 3-layer active cell 50). Air and fuel are fed into the device 10 through the passive passages that are fluidicly coupled to the active passages that feed the active cells 50. Thus, a fuel passage 14 and an oxidizer passage 20, as referred to herein, include both the passive and active portions of the passages.

As discussed above, it is desirable to make the electrolyte 28 as thin as possible. However, as the electrolyte 28 is made thinner, the support of the structure can be compromised, and distortion of the active portion of fuel and air passages 14, 20 that feed the anodes 24 and cathodes 26 can occur at one or more locations within the active cell 50, as well as distortion of the passive portions of the passages 14, 20. These distortions in the passages 14, 20 may lead to leaks that degrade the performance of the affected active cell 50 and of the overall device 10.

One advantage of the multilayer fuel cell devices developed by the present inventors is that many active cells 50 can be provided within a single monolithic device, including multiple cells along a single active layer and stacks of active layers one upon another, which can be connected in various parallel and series arrangements, leading to a single device with high output. If one area of one cell distorts, there are still many other cells that produce power, such that the multilayer fuel cell devices are still superior to single cell tubular devices or stacked devices that are not monolithic. However, the more layers that are incorporated, the higher the chance for multiple distortions throughout the device.

Therefore, there is a need to provide thin electrolyte layers while still providing the needed support to prevent distortion of the gas passages within a monolithic multilayer fuel cell device.

SUMMARY OF THE INVENTION

According to one embodiment, a method of making a monolithic fuel cell device is provided, comprising forming an anode layer by dispensing a first paste of anode material around a first plurality of spaced-apart removable physical structures to at least partially surround each of the first plurality of spaced-apart removable physical structures with the anode material and drying the first paste, and forming a cathode layer by dispensing a second paste of cathode material around a second plurality of spaced-apart removable physical structures to at least partially surround each of the second plurality of spaced-apart removable physical structures with the cathode material and drying the second paste. An electrolyte layer is provided in a multi-layer stack between the cathode layer and the anode layer, wherein an active cell portion of the multi-layer stack is formed by the anode layer in opposing relation to the cathode layer with the electrolyte layer therebetween. The multi-layer stack is laminated, and then the first and second plurality of removable physical structures are pulled out of the laminated multi-layer stack to reveal spaced-apart active passages formed through each of the anode layer and the cathode layer. Finally, the laminated multi-layer stack is sintered to form an active cell comprising the spaced apart active passages embedded in and supported by the sintered anode material and sintered cathode material.

According to another embodiment, a method of making a monolithic fuel cell device is provided, comprising forming an anode layer by dispensing a first paste of anode material around a first plurality of removable physical structures to at least partially surround each of the first plurality of removable physical structures with the anode material and drying the first paste, and forming a cathode layer by dispensing a second paste of cathode material around a second plurality of removable physical structures to at least partially surround each of the second plurality of removable physical structures with the cathode material and drying the second paste. Each of the first and second plurality of removable physical structures have an elongate length and are positioned in the respective anode and cathode layer in parallel in the length direction and physically spaced apart from each other in a direction transverse to the length direction. An electrolyte layer is further positioned in a multi-layer stack between the cathode layer and the anode layer, wherein an active cell portion of the multi-layer stack is formed by the anode layer in opposing relation to the cathode layer with the electrolyte layer therebetween. A third paste of ceramic material is dispensed around the first and second plurality of removable physical structures adjacent to the anode and cathode materials to surround each of the first and second plurality of removable physical structures with the ceramic material and drying the third paste to form a passive support portion adjacent the active cell portion in the multi-layer stack. The multi-layer stack is laminated, and then the first and second plurality of removable physical structures are pulled out of the laminated multi-layer stack to reveal spaced-apart passages formed in the passive support portion and transitioning through each of the anode layer and the cathode layer in the active cell portion. Finally, the laminated multi-layer stack is sintered to form an active cell with an adjacent ceramic passive support structure with the spaced-apart passages embedded in and supported by the sintered ceramic material, anode material and cathode material.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Reference may be made to the following patents and publications by the same inventors, which describe various embodiments of a multilayer Fuel Cell Stick™ device 10 (et al.), the contents of which are incorporated herein by reference: U.S. Pat. Nos. 8,278,013, 8,227,128, 8,343,684, and 8,293,415, and U.S. Patent Application Publication Nos. 2010/0104910 and 2011/0117471. The inventive structures and/or concepts disclosed herein may be applied to one or more of the embodiments disclosed in the above-reference published applications.

Various material terms will be used interchangeably, regardless of the stage of the material during manufacturing. For example, anode 24, anode layer 24, anode material 24, etc. all refer to the anode itself or the layer in which one or more anodes are positioned, irrespective of whether the anode material is in the form of a paste, a preform layer, a sintered layer, an initial green state, or a final fired state.

Figure 1:
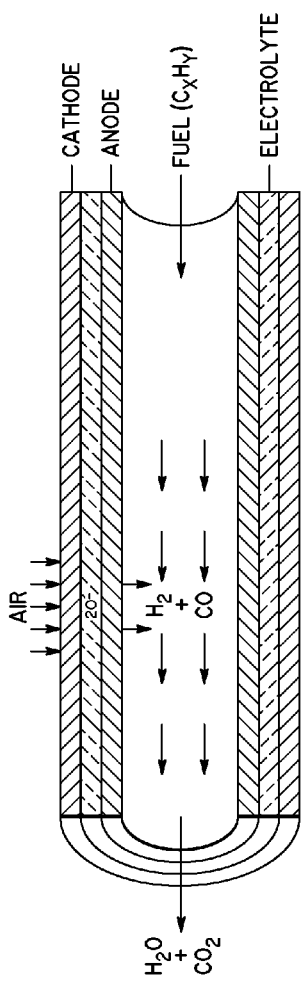
FIG. 1 is a schematic view of a tubular solid oxide fuel cell device of the prior art.
Figure 2:
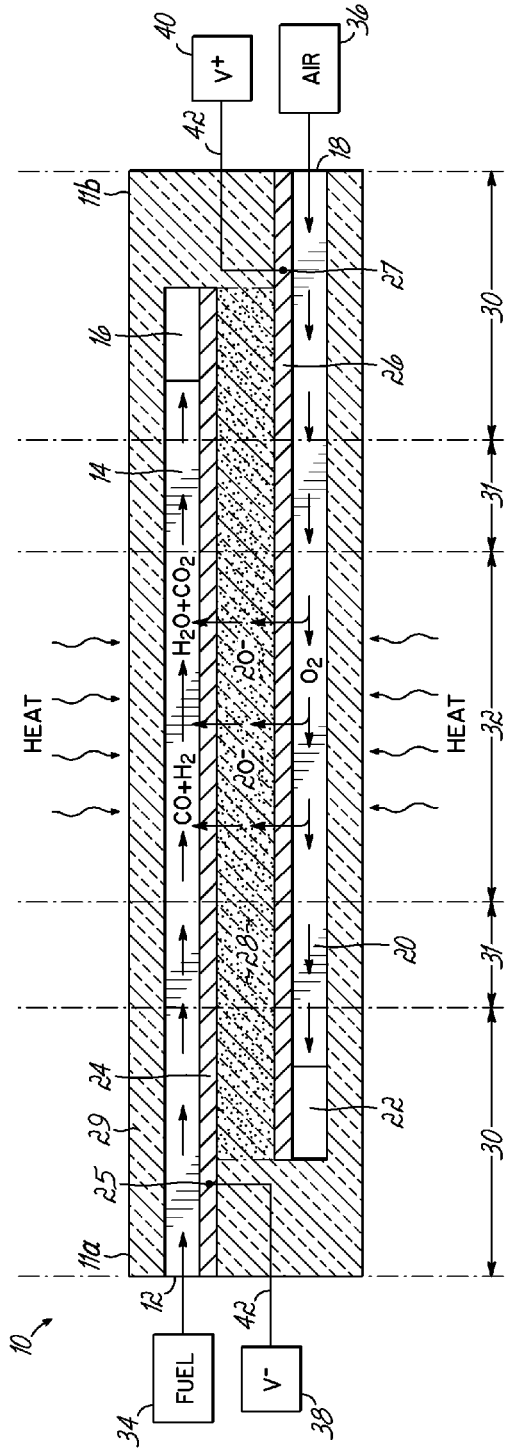
FIG. 2 is a schematic side cross-sectional view of a solid oxide Fuel Cell Stick™ device of the prior art.
Figure 3:
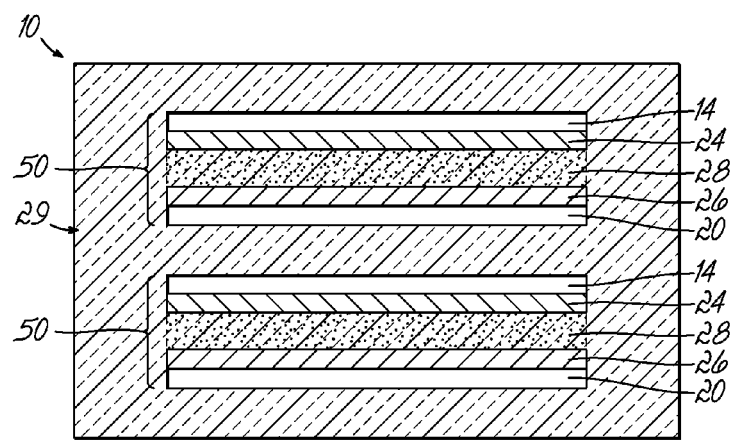
FIG. 3 is a schematic end cross-sectional view of a solid oxide Fuel Cell Stick™ device of the prior art.

In accordance with the present invention, to form the passive and active passages in multilayer fuel cell devices, removable physical structures, such as wires, are placed in the anode and cathode layers of the device as the layers are assembled in the green state. The removable physical structures travel from one end of the device, through the active area, and are spaced apart from one another with the anode or cathode material therebetween. Previous designs used removable physical structure at the ends of the device to form the passive passages, which were coupled to larger areas of organic sacrificial material that were used inside the device to form the active passages. The wires were simply placed between preformed sheets of green ceramic material with one end in contact with the sheet of sacrificial material and the other end extending outside the end of the device. After lamination, during which the preformed sheets conform to the shape of the physical structures, the removable physical structures were pulled out, and then the device was co-fired, allowing the sacrificial material to burn out and exit the end of the device through the passive passages and/or through other temporary bake-out ports in the sides. Despite embodiments that use ceramic balls in the active area to help support the active passages, the large flat active passages, as shown in FIG. 3, are still only partially supported at best and sometimes distort as the sacrificial material bakes out. As explained above, distortions have occasionally led to leaks, which have degraded the performance of the cell.

In the present method, the active area is assembled with removable physical structures, such as fine wires, for example, 0.01 inch (0.254 mm), that are spaced apart and surrounded by solid material. In other words, the removable physical structures are at least partially surrounded by solid material so as to embed them within a layer of green material, rather than placed between preformed layers. The removable physical structures will be referred to as wires, interchangeably for ease of discussion, with the understanding that the invention is not limited to wires as the only possible removable physical structures. Removable physical structures are distinguished from sacrificial materials that burn out at elevated temperatures, and refer instead to solid structures that are pulled out of the device.

Figure 4:
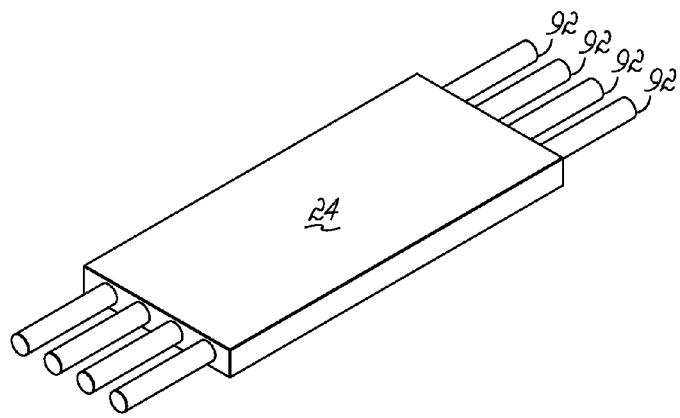
FIG. 4 is a perspective view of an anode layer formed by an embodiment of a method of the invention.

FIG. 4 depicts in perspective view a green layer of anode material 24 having a plurality of wires 92 extending all the way through and surrounded by the anode material 24. The use of wires 92 to form spaced apart passages 14, 20 in the active area 50 is advantageous because the active area 50 then has a solid support for the gas passages. The solid material is first made as a paste, filled with anode, cathode or ceramic particles, and then dispensed and dried around the wires 92 to fully support the wires. The solid material is necessarily porous for at least a portion of the anode 24 and cathode 26. The wires 92 can be placed in parallel, if desired, and then the material is dispensed over the top of the wires. A vacuum can be pulled after dispensing the paste, in order to remove any air pockets below the wires so that the wires 92 are completely surrounded. Alternatively, a layer of paste can be deposited, then the wires 92 positioned, and then more paste applied. Thus, a layer containing the wires 92 may be formed separately, for example using a mold and paste materials, and then dried to form a wire-containing preformed sheet, which preformed sheets can then be stacked. Additionally or alternatively, the paste for one layer can be applied on top of a preceding layer in a manner that embeds the wires 92 in the paste of that layer, and that layer is then dried in place in the stack. Thus, the entire stack can be built sequentially on a surface in such a way that each layer is built and dried, and then another layer is put on top and dried, or each layer can be premade and treated as preforms, and the stack built up from many different pre-made sub components, or any combination of these two techniques can be used to assemble a complete device stack.

Figure 5:
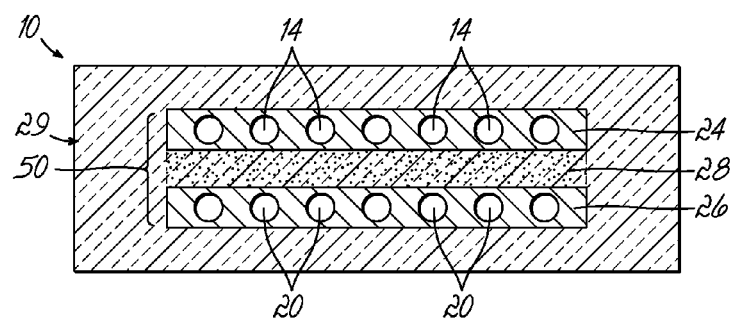
FIG. 5 is a schematic end cross-sectional view of a device formed according to an embodiment of a method of the invention.
Figure 6:
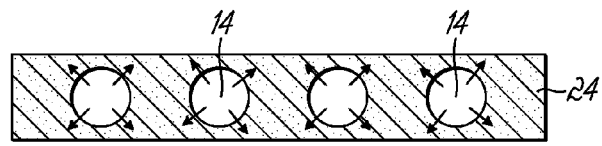
FIGS. 6-9 are schematic cross-sectional views of anode layers formed by embodiments of a method of the invention.

Once the device stack is formed, it is laminated, and then the wires 92 are removed. The layer-by-layer dimensions are better maintained during lamination with the present invention because the green preform layers already contain the wires 92 with the electrode material surrounding and conforming to the wire shape, such that the green layers need not conform around the wires 92 as the layers are pressed together. The result, for a single active cell 50, is shown in cross-section in FIG. 5, after the wires 92 are pulled out, and after the porous anode and cathode materials are fired. Rather than a large flat passage 14 adjacent the anode 24, as shown in FIG. 3, the device in FIG. 5 includes a plurality of small round fuel passages 14 embedded within the anode 24, and the same is true for the cathode 26 and oxidizer passages 20. Round wires are not required, as other shapes can be used. Because the wires 92 are removed before baking the stack, binder removal from the porous materials and from any sacrificial layers will proceed more quickly because exit passages for the binder are already present. FIG. 6 shows, for an anode 24, how the gas in operation of the device 10 can flow through the fine fuel passages 14, and then travel through the porous anode 24 to reach an electrolyte area 28. A single electrode can also serve two electrolyte layers 28 on either side.

Figure 7:
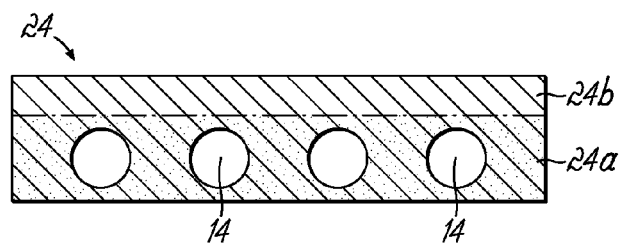
Figure 8:
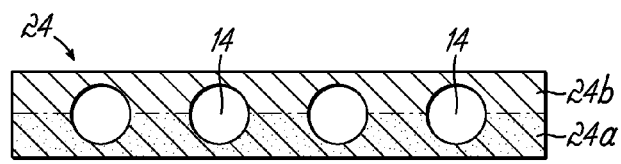

In the active cell 50, different combinations of materials can be used in combination with the wires 92. FIG. 7 depicts, for an anode layer 24, a combination of a porous anode 24a with the fuel passages 14 embedded therein and a non-porous anode 24b adjacent thereto (and opposite the electrolyte, not shown). FIG. 8 is similar to FIG. 7 but with the fuel passages 14 formed along the interface between the porous anode 24a and the non-porous anode 24b. With paste materials, a layer of the porous anode paste can be laid down first, followed by laying the wires 92 onto the paste and pushing them halfway into the paste, and then applying the non-porous anode paste over the wires. Depending on whether and how far the wires are pushed into the porous layer will determine the position of fuel passages at the interface, e.g., off-center and residing mostly in the porous layer, off-center and residing mostly in the non-porous layer, or centered halfway in each layer.

Figure 9:
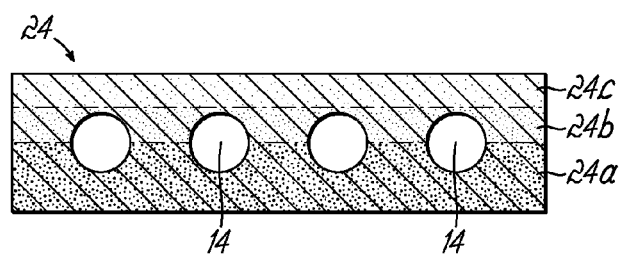

FIG. 9 shows how the paste materials can transition from one layer to the next to give a grading in the thickness direction (z direction), for example, a graded porosity with layer 24a being highly porous, layer 24b having medium porosity, and layer 24c have low porosity, for example in a direction away from the electrolyte. While not shown, rather than a multi-layer anode 24 surrounding the wires 92, a multi-layer structure can include combinations of electrode and ceramic layers, or a grading in which ceramic material is mixed with electrode material to transition from pure electrode to pure ceramic. Each layer in a multi-layer structure can be tailored to perform different functions, such as one material being anode/cathode, and the other being ceramic or YSZ; porous versus non-porous; larger versus smaller pores; chemical composition variations; relative electrical conductivity variations; relative ionic conductivity variations; variations in the ability to bond to surrounding materials; or any other physical or chemical variation.

When coating the wires with the desired material to form a layer having the plurality of spaced-apart passages embedded therein, the material can completely cover or not completely cover the wires, and the proper choice of the coating conditions can help achieve the optimal performance. Having a majority of the wire 92 surrounded by the material of the layer achieves the objective of providing support for the structure.

If the surrounding material does not exceed the top and bottom of the wires having a round shape, the intervening support material is a pillar shaped structure. This is the minimum structure necessary to give a solid support structure in the active area, such that it is not required that the passages be completely encompassed within the electrode, only mostly encompassed by virtue of being essentially sandwiched between support structures. The support material can meet the wire exactly at the top and bottom surfaces or the support material can be recessed on both sides of the wires, either way forming a pillar structure. Additionally, an asymmetric structure can be formed where one side of the wires is exceeded and one side is not. By way of example, the pillar form, and in particular the recessed pillar form, can be created by using a paste that becomes much thinner as the solvent dries out of the polymer matrix or by shaving the top surface with a thin razor blade and distorting down between the wires.

Figure 10:
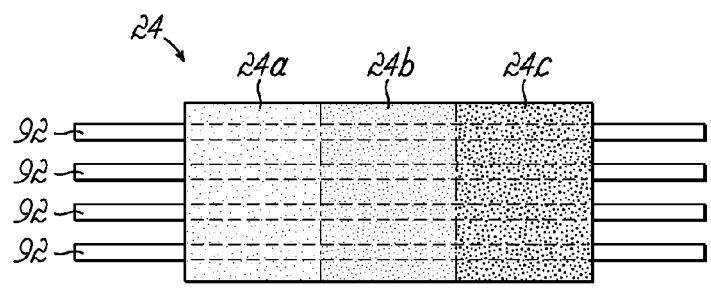
FIG. 10 is a top view of an anode layer formed by an embodiment of a method of the invention.

As opposed to varying the material composition in the thickness direction of the wires, FIG. 10 shows variation down the length of the wires 92 for an anode 24, in particular, an anode layer 24a along a first length portion, an anode layer 24b along a second length portion, and an anode layer 24c along a third length portion. Any number of different material types is possible. Variations of anodes, ceramics, and cathodes down the length of the wires 92 are also possible, such that the structure could contribute to the formation of a series fuel cell travelling down the length direction. Another variation is to replace the anode layers 24a and/or 24c with sacrificial material to form sections having large volume flow paths in combination with the supported flow sections, or to insert sacrificial segments that will form exit paths to the sides of the device 10.

With respect to the wires 92 or other physical structures, variations are possible in terms of wire diameters, wire materials, and wire properties. The wires can be 0.02 inch, 0.01 inch, 0.005 inch, or 0.002 in, for example. The wires can be made of stainless steel, carbon steel, nickel, titanium, or any other appropriate material. The wires can be spring metal, annealed, flexible and have varying degrees of strength. The wires can be straight or curved, as discussed further below. The wires can be round, oval, semi-circular, square, rectangular, or any other shape, as desired. The plurality of wires in a single layer need not all be of the same shape or dimension, and can be different in one layer versus another layer. Additionally, the wires can change in dimension and/or shape as they travel down the length of the device. For example, a wire can have a first diameter along the length of the passive area of the device and gradually or sharply decrease to a second diameter in the active area of the device, for example, a smaller second diameter. In another example, the wire can have a first shape along the length of the passive area of the device and gradually or sharply change to a second shape in the active area of the device, such as a first round shape and a second semi-circular shape or a second oval shape. The changes in diameter and shape may be designed to achieve objectives in gas flow properties and/or to achieve less resistance to the wires being removed after lamination. It may also be advantageous to heat the device after lamination to facilitate the wire removal, for example, to about 85° C., although other temperatures are contemplated. In one embodiment, the temperature of the device is raised to above the glass transition temperature ($T_g$) of the organic materials of the stick to dramatically soften the material, allowing easy removal of the wires. Additionally, the wires may be coated, as necessary with a release agent. However, the use of heat may make the use of release agents unnecessary. Wires may be used to form any combination of input passages, active passages, and exhaust passages. Further, within a single layer, such as an anode layer 24, the wires 92 may be arranged in parallel in a single layer, or multiple spaced layers. The size of the wires, and thus the size of the formed passages, may also be varied in the multiple spaced layer, for example, a row of smaller diameter passages could be formed in anode layer 24b of FIG. 7, and this row could be aligned or offset with respect to the passages in anode layer 24a, as desired.

Various methods are possible for connecting the gas supplies to the fuel and air passages. In an elongated device, a fuel supply can be coupled to one end, and an air supply to the opposite end, for example, by placing flexible supply tubes over the ends. In such embodiments, the fuel entering one end would have to exit the device at a point before reaching the opposite end, since the opposite end is coupled to the air supply. Thus, side exits or vertical exits have been contemplated in previous designs. When using wires 92 to form the passages 14, 20 to and through the active area 50, the wires for forming the fuel passages, 14, for example, can extend lengthwise from a fuel input end of the device and terminate at the conclusion of the active area, or can proceed into the opposite passive area but stop short of the opposite air input end. A side exit path can then be formed using sacrificial material or additional wires in contact with the lengthwise wires, such as at the ends of the wires, and extending widthwise to the side of the device.

Alternatively, the wires can extend through the entire length of the device, such that both the fuel and oxidizer passages 14, 20 extend from a first end 11a to a second end 11b, but then one of the set of passages 14 or 20 is sealed off at each end, such as by injecting a small amount of ceramic or glass paste into the passages at the ends to plug them and seal them off, or by temporarily plugging the passages to be kept with short wires and painting a paste of ceramic or glass over the passages to be sealed, drying the paste, then removing the temporary plugs. Exit passages to the sides or vertically would still need to be formed then ahead of the plugs. In yet another alternative, where the wires extend the full length of the device, supply of the gases may be made by a plurality of supply tubes, for example, ceramic tubes, that are sized to be inserted into the respective plurality of passages, in typical manifold fashion, but advantageously outside the furnace in the cold end region of the device.

Figure 11A:
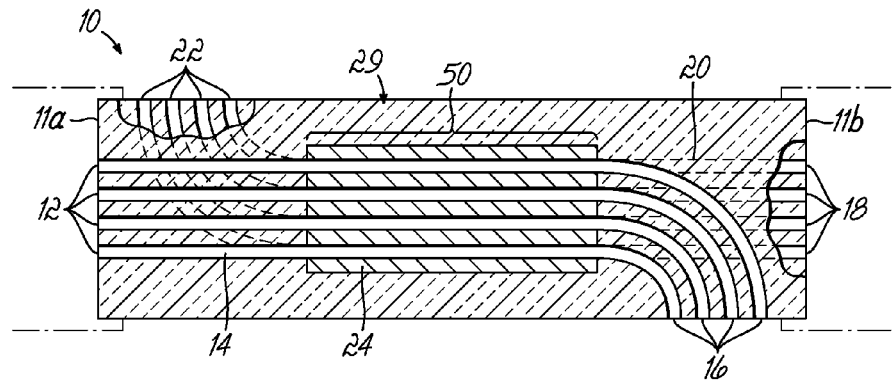
FIG. 11A is a partial cut-away top cross-sectional view of a device formed by an embodiment of a method of the invention.

In alternative embodiments, shown in FIGS. 11A-11B, 12A-12B, 13 and 14, curved wires can be used to form the passages 14, 20. In FIG. 11A, for forming the anode layer 24, the wires 92 are straight at end 11a until they reach the end of the active area 50, then they curve toward one side of the device 10 to form the fuel output 16 at the side. For the cathode layer 26, the wires 92 are straight from the opposite end 11b, until they reach the end of the active area 50, then they curve toward one side of the device 10 to form the oxidizer output 16 at the side. With the anode layers 24 and cathode layers 26 stacked together, a device 10 may be formed as shown. Supply tubes (partially depicted in phantom) can be fitted over each end 11a, 11b for supplying the fuel and air, respectfully, to inlets 12 and 18, while the spent gases exit out the sides of the device 10 from outputs 16, 22 before reaching the ends 11a, 11b.

Figure 11B:
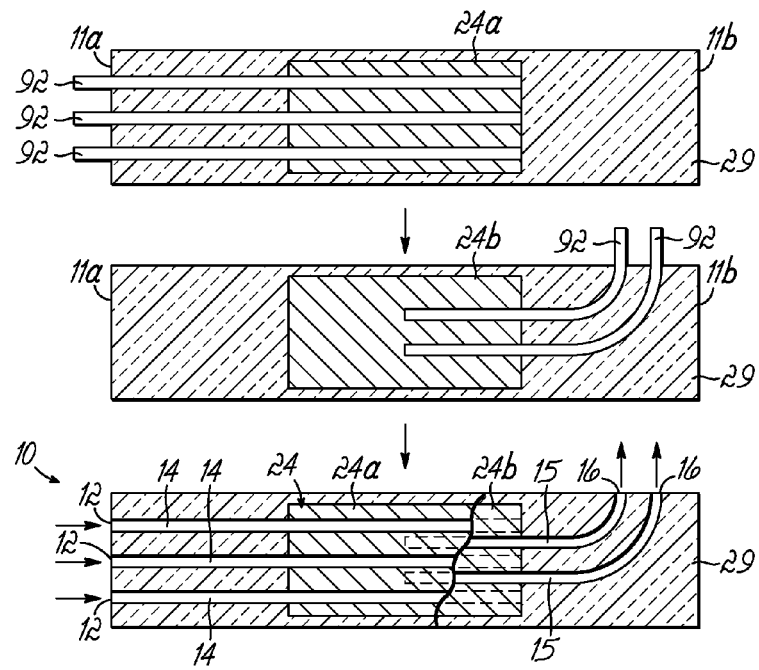
FIG. 11B is a sequence of schematic partial cut-away top cross-sectional views depicting assembly of an anode layer formed by an embodiment of a method of the invention.

In FIG. 11B, a two-layer electrode structure can be used to form the spaced-apart passive and active passages 14, 20 in one layer and spaced-apart exhaust passages 15, 21 in the other layer. In anode layer 24a, straight wires 92 are used from the end 11a to the end of the active area 50 to form fuel passage 14. A curved wire 92 is used in anode layer 24b to form exhaust passages 15 from the active area 50 to the side for the outlet 16 of spent fuel. The exhaust passages 15 (and 21, not shown) need not extend through the entire active area 50, but can begin within the active area 50, such as halfway into the active area 50. As shown, the exhaust passages 15 are offset from the active passages 14, but this is not required.

Figure 12A:
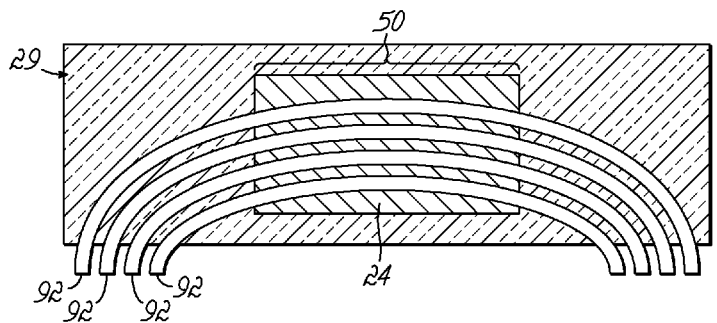
FIG. 12A is a schematic top cross-sectional view of an anode layer formed by an embodiment of a method of the invention.
Figure 12B:
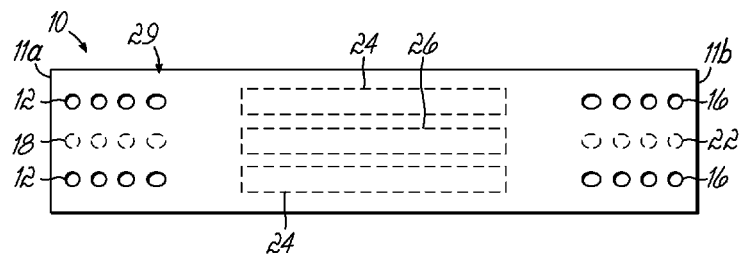
FIG. 12B is a schematic side view of a device formed according to an embodiment of a method of the invention.

In FIGS. 12A-12B, showing an anode layer 24 in FIG. 12A and a resulting device 10 in FIG. 12B, the wires 92 curve the entire length of the device 10 from the input through the active area 50 and to the output, so as to form inputs 12, 18 and outputs 16, 22 in the sides of the device 10. While this may not be a preferred embodiment in terms of connecting the fuel and air supplies, manifold-type connections are nonetheless feasible.

Figure 13:
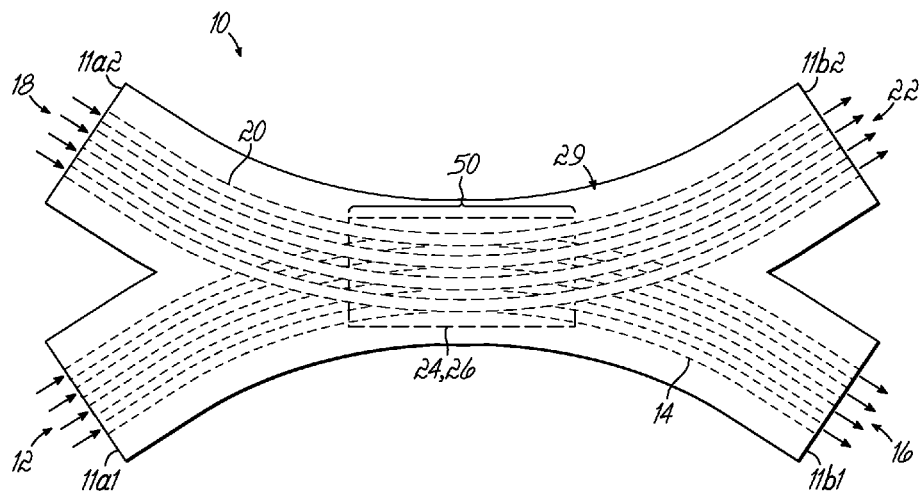
FIGS. 13 and 14 are schematic top views of devices formed by embodiments of a method of the invention.

To better provide for separate fuel and air connections, FIG. 13 uses the same curved wires 92 as in FIG. 12A, but splits the ends 11a, 11b of the device 10 to form a pair of first end portions 11a1 and 11a2 and a pair of second end portions 11b1 and 11b2. This construction is made possible by the fact that the layers are assembled from the green state, and thus the green layers can be molded, cut and/or shaped to have the desired form. The pair of first end portions 11a1, 11a2 can be coupled to fuel and air supplies to feed gases to the fuel and air inputs 12, 18, respectively, and the spent gases can exit from outputs 16, 22, respectively, in the pair of second end portions 11b1, 11b2.

Figure 14:
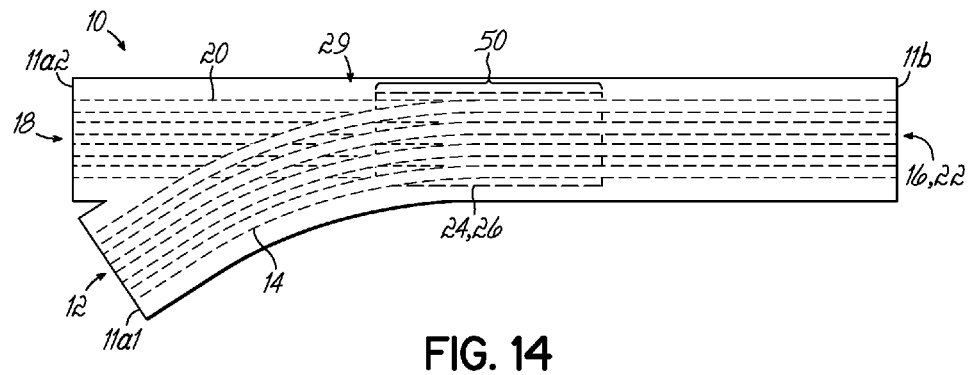

FIG. 14 depicts a combination of the various embodiments above, utilizing partially curved wires, straight wires, and a split end. A pair of first end portions 11a1 and 11a2 are formed to accommodate separate fuel and air connections to inputs 12, 18, respectively, with only first end portion 11a1 being curved. Wires 92 are used that curve from first end portion 11a1 into the active area 50 then straighten and exit at end 11b. Straight wires 92 are used that enter at first end portion 11a2 and exit at end 11b, such that both outputs 16 and 22 are at the single end 11b of the device.

Figure 15:
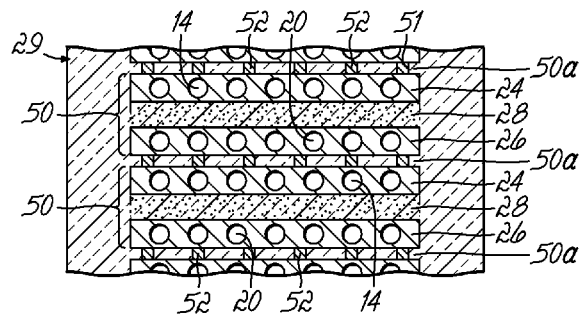
FIG. 15 is a schematic end cross-sectional view of a device formed according to an embodiment of a method of the invention.

FIG. 15 shows another embodiment for building a series fuel cell structure in the vertical (thickness) direction. This can dramatically reduce the path length for the interconnect compared to other designs because the distance from one active cell to the next becomes very short and very wide, and this gives the lowest resistance combination. In addition, the use of interconnect material, and possibly precious metal, is reduced overall.

FIG. 15 depicts in schematic cross-section two active cells 50 stacked in series, but many active cells 50 can be stacked one upon another by this method. The anode layers 24 and cathode layers 26 are formed as described above, for example, as shown in FIG. 6, and stacked with intervening electrolyte layers 28 to form a three-layer active cell stack 50 of anode 24/electrolyte 28/cathode 26. A non-conductive interconnect layer 50a is positioned between each active cell stack 50, with each interconnect layer 50a having a plurality of conductive vias 52 extending there-through to make electrical contact with the cathode 26 of one active cell 50 and the anode 24 of the next active cell 50. To make the interconnect layer 50a, a green sheet of non-conductive ceramic material can be hole-punched to provide via holes 51, and conductive paste, for example, containing precious metal, can be filled into the via holes 51 for making the electrical connection with the conductive vias 52.

Figure 16:
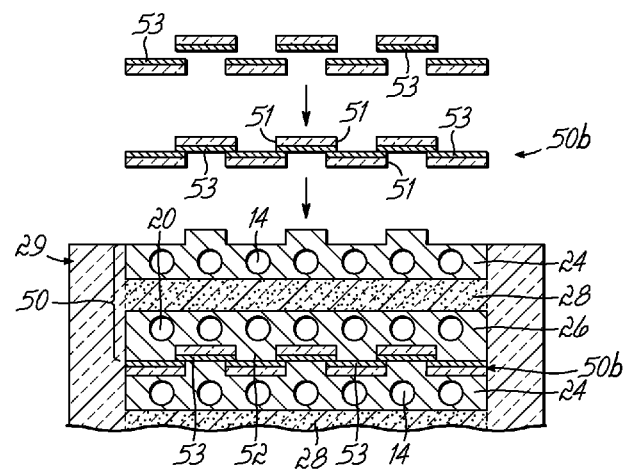
FIG. 16 is a sequence of schematic end cross-sectional views depicting assembly of an interconnect layer used in a device formed by an embodiment of a method of the invention.

The use of filled or plugged via holes can provide a potential source of gas leaks, which negatively affect device performance, so an alternate embodiment is shown in exploded view in FIG. 16. As with FIG. 15, active cell stacks 50 are formed, but a variation is used to electrically connect the active cells 50 in series. In particular, the interconnect layer 50b is made of more than one ply (in this case two) where the via holes 51 are offset. This offset technique can prevent or reduce the leakage of gas from one side to the other. Instead of a single sheet of non-conductive material, two non-conductive sheets are provided with via holes 51, and a conductor layer 53 is printed on one side of each sheet and they are stacked with the printed sides facing each other, with the via holes 51 offset so that they do not overlap. In this embodiment, there is no need to actually fill the via holes 51 with interconnect material, as they can be filled instead with anode 24 or cathode 26 material, as shown. This approach then saves on the use of precious metal. In the case of the cathode side, the material (LSM, for example) can be made dense so that it contributes to leak-prevention.

In the embodiments of FIGS. 15 and 16, the via holes 51 can be large or small, and can be plenty or few. By way of example, and not limitation, via holes 51 can be 0.1 inch (2.54 mm) in diameter, or can be 25 μm.

Figure 17:
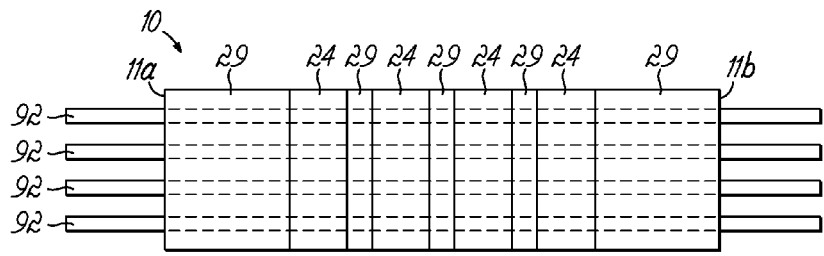
FIG. 17 is a schematic top view of an anode layer formed by an embodiment of a method of the invention.
Figure 18:
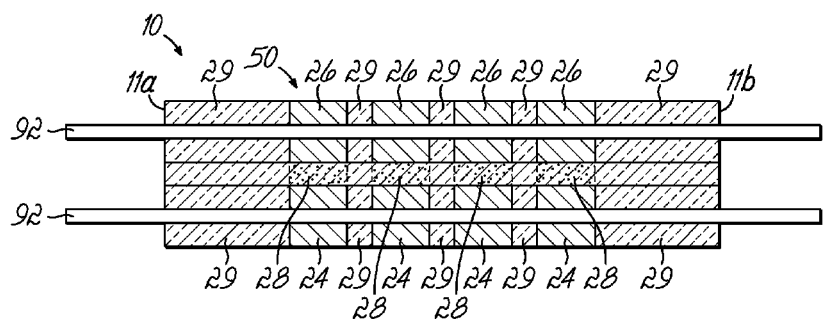
FIG. 18 is a schematic side cross-sectional view of a device formed according to an embodiment of a method of the invention.

It was discussed above that the paste material deposited around the wires 92 can be varied in the length direction, for example, as shown in FIG. 10. This concept can be used to create a series design down the length of the device 10, rather than vertically as shown in FIG. 15. In FIG. 17, a top view depicts an anode layer having alternating segments of ceramic support material 29 and anode material 24 embedding the wires 92. A similar cathode layer may be formed with cathode material 26, and these layers may be stacked with the segments of anodes 24 and cathodes 26 aligned and with an intervening electrolyte layer 28 to form an active cell layer having a successive series of active cells 50 down the length, as shown in side view in FIG. 18. The series connections may be made on the sides of the device 10 if all or a portion of the anodes 24 and cathodes 26 extend the full width or at least to one side of the device 10, or internally using previously disclosed methods in prior applications cited above, or methods disclosed herein.

Figure 19:
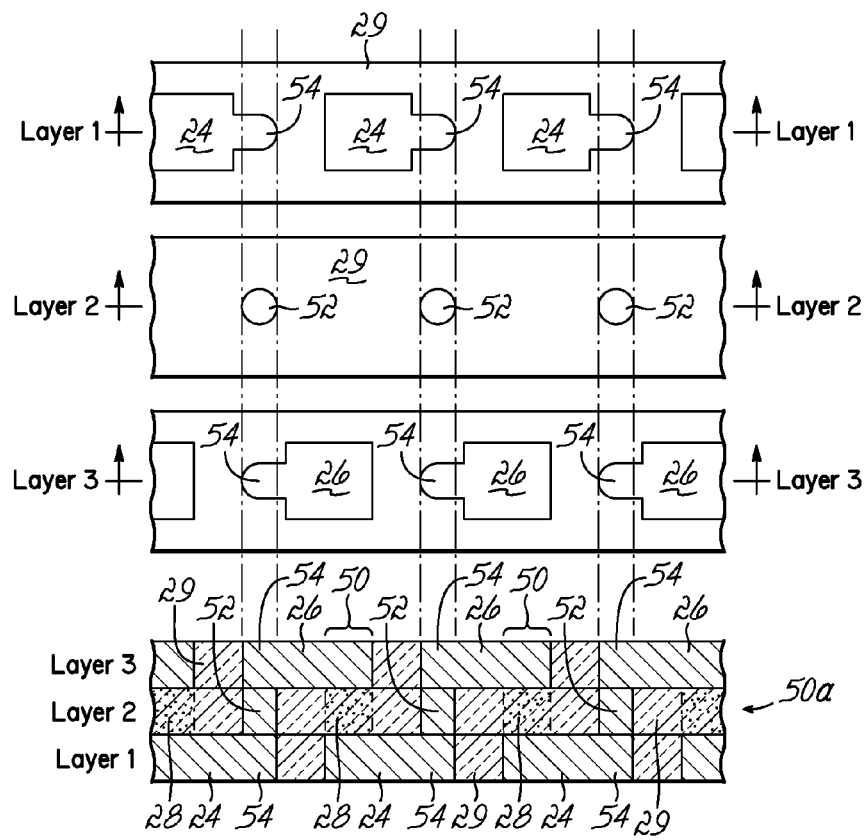
FIG. 19 is a series of schematic top views and a schematic side cross-sectional view depicting assembly of a series connection in a device formed by an embodiment of a method of the invention.
Figures 20A, 20B:
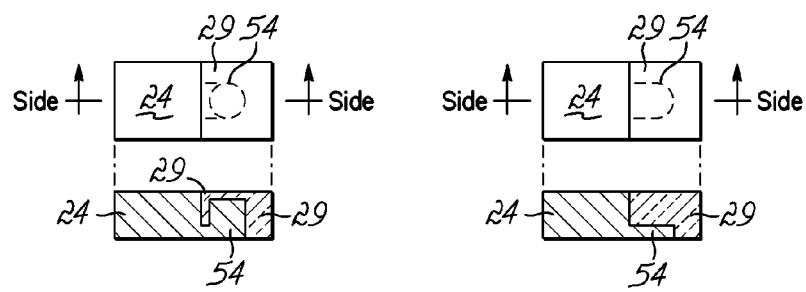
FIGS. 20A and 20B are paired top and schematic side cross-sectional views depicting alternative anode interconnect tabs in the embodiment of FIG. 19.

One method for forming internal series connections is to include an interconnect tab 54 for each electrode segment, as shown in FIG. 19 (wires not shown). The exploded view depicts each of the anode layer (layer 1), a combination electrolyte 28/interconnect layer 50a containing both the electrolyte 28 and the conductive vias 52 (layer 2), and the cathode layer (layer 3), in top view and in alignment for stacking, and then in side view as stacked. The wires are not shown, but would be extending through each of layers 1 and 3. The interconnect tab 54 of the anode 24 of one active cell 50 is aligned with the interconnect tab 54 of the cathode 26 of the next adjacent active cell 50, and the conductive via 52 of interconnect layer 50a is aligned with both, thereby making the series connection between the adjacent active cells 50. Alternative interconnect tabs 54 are depicted schematically in FIGS. 20A and 20B, showing both a top view and a side view. In FIG. 20A, the tab is notched, which provides an interlock between the anode segment 24, the ceramic support material 29 and the interconnect tab 54, which may contribute to leak prevention. In FIG. 20B, the interconnect tab 54 is a thin extension only at the surface that interfaces with the interconnect layer 50a, thereby minimizing the material used for the electrical connection.

Figure 21A:
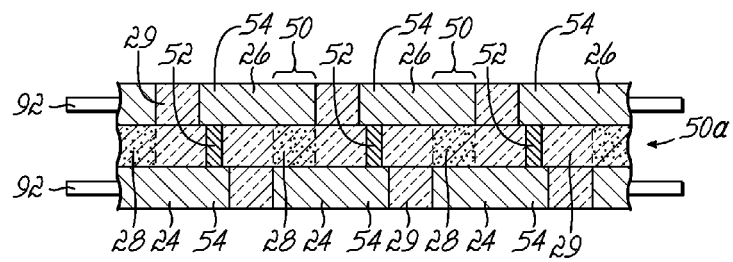
FIGS. 21A and 21B are a schematic side cross-sectional view and a schematic partial cut-away top cross-sectional view, respectively, of a series connection in a device formed by an embodiment of a method of the invention.
Figure 21B:
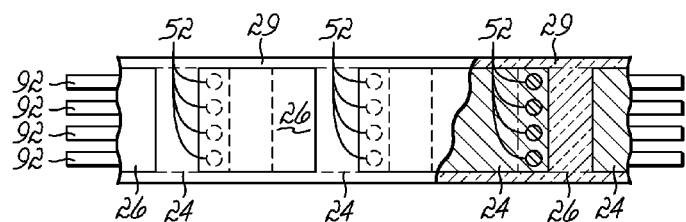

Referring to FIGS. 21A and 21B, in side view and top view, respectively, another series structure is depicted using alternating electrode and ceramic support segments. In the stacking of the layers, the anode segments in one layer are offset with respect to the cathode segments in the other layer, with the combination electrolyte 28/interconnect layer 50a therebetween. The edge of the anode 24 of one active cell 50 is aligned with the edge of the cathode 24 of the next adjacent active cell 50 to provide a small overlapping region, and the conductive vias 52 of interconnect layer 50a are then aligned with that overlapping region. This design then eliminates the need for the interconnect tabs 54. Rather than the interconnect layer 50a, the interconnect layer 50b may be used instead, which is formed from two sheets with the printed conductor layer 53 therebetween.

The various series designs enable any number of active cells, whether situated in a single active layer sequentially down the length, or vertically by stacking active cells on top of each other, or a combination of both. Thus, small devices or large devices can be provided with relatively high voltage. For example, a handheld electronic device could be provided with the design of FIGS. 21A-21B to give low wattage with a high voltage, for example, 0.25 W and 3.6 V.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope of the general inventive concept.

What is claimed is:

1. A method of making a monolithic fuel cell device, comprising:
    forming an anode layer by dispensing a first paste of anode material around a first plurality of spaced-apart removable physical structures to at least partially surround each of the first plurality of spaced-apart removable physical structures with the anode material and drying the first paste;
    forming a cathode layer by dispensing a second paste of cathode material around a second plurality of spaced-apart removable physical structures to at least partially surround each of the second plurality of spaced-apart removable physical structures with the cathode material and drying the second paste;
    positioning an electrolyte layer in a multi-layer stack between the cathode layer and the anode layer, wherein an active cell portion of the multi-layer stack is formed by the anode layer in opposing relation to the cathode layer with the electrolyte layer therebetween;
    laminating the multi-layer stack;
    pulling the first and second plurality of removable physical structures out of the laminated multi-layer stack to reveal spaced-apart active passages formed through each of the anode layer and the cathode layer; and
    sintering the laminated multi-layer stack to form an active cell comprising the spaced apart active passages embedded in and supported by the sintered anode material and sintered cathode material,
    wherein forming one or both of the anode layer and cathode layer includes dispensing the first or second paste with a varying composition in the thickness direction of the removable physical structures, wherein the variation in composition is selected from amount of porosity, size of pores, chemical composition, relative electrical conductivity, relative ionic conductivity, bonding properties, ratio of anode or cathode material to ceramic material, or a combination thereof, and wherein the varying composition includes a graded porosity with the porosity decreasing in a thickness direction away from the electrolyte layer.

2. The method of claim 1, further comprising dispensing a third paste of ceramic material around the first and second plurality of spaced-apart removable physical structures adjacent to the anode and cathode materials to at least partially surround each of the first and second plurality of spaced-apart removable physical structures with the ceramic material and drying the third paste to form a passive support portion adjacent the active cell portion in the multi-layer stack, wherein the sintering further forms a passive support structure comprising spaced apart passive passages embedded in and supported by the sintered ceramic material and that transition integrally to the active passages within the active cell.

3. A method of making a monolithic fuel cell device, comprising:
forming an anode layer by dispensing a first paste of anode material around a first plurality of spaced-apart removable physical structures to at least partially surround each of the first plurality of spaced-apart removable physical structures with the anode material and drying the first paste;
forming a cathode layer by dispensing a second paste of cathode material around a second plurality of spaced-apart removable physical structures to at least partially surround each of the second plurality of spaced-apart removable physical structures with the cathode material and drying the second paste;
positioning an electrolyte layer in a multi-layer stack between the cathode layer and the anode layer, wherein an active cell portion of the multi-layer stack is formed by the anode layer in opposing relation to the cathode layer with the electrolyte layer therebetween;
laminating the multi-layer stack;
pulling the first and second plurality of removable physical structures out of the laminated multi-layer stack to reveal spaced-apart active passages formed through each of the anode layer and the cathode layer; and
sintering the laminated multi-layer stack to form an active cell comprising the spaced apart active passages embedded in and supported by the sintered anode material and sintered cathode material,
wherein forming one or both of the anode layer and cathode layer includes forming a multi-layer electrode structure having at least a first sub-layer of porous anode or cathode paste material and a second sub-layer of non-porous anode or cathode paste material dispensed over the first sub-layer, wherein the positioning of the electrolyte layer is adjacent the first sub-layer, and
wherein the first sub-layer is dispensed around one side of the respective first or second plurality of spaced-apart removable physical structures and the second sub-layer is dispensed around the opposing side of the respective first or second plurality of spaced-apart removable physical structures such that, after sintering, the spaced apart active passages are partially embedded in and supported by the sintered porous anode or cathode material on one side and partially embedded in and supported by the sintered non-porous anode or cathode material on the opposing side.

4. A method of making a monolithic fuel cell device, comprising:
forming an anode layer by dispensing a first paste of anode material around a first plurality of spaced-apart removable physical structures to at least partially surround each of the first plurality of spaced-apart removable physical structures with the anode material and drying the first paste;
forming a cathode layer by dispensing a second paste of cathode material around a second plurality of spaced-apart removable physical structures to at least partially surround each of the second plurality of spaced-apart removable physical structures with the cathode material and drying the second paste;
positioning an electrolyte layer in a multi-layer stack between the cathode layer and the anode layer, wherein an active cell portion of the multi-layer stack is formed by the anode layer in opposing relation to the cathode layer with the electrolyte layer therebetween;
laminating the multi-layer stack;
pulling the first and second plurality of removable physical structures out of the laminated multi-layer stack to reveal spaced-apart active passages formed through each of the anode layer and the cathode layer; and
sintering the laminated multi-layer stack to form an active cell comprising the spaced apart active passages embedded in and supported by the sintered anode material and sintered cathode material,
wherein forming one or both of the anode layer and cathode layer includes forming a multi-layer electrode structure having a plurality of sub-layers each with a differing porosity, with the multi-layer electrode structure decreasing in porosity in a thickness direction away from the electrolyte layer.

5. A method of making a monolithic fuel cell device, comprising:
forming an anode layer by dispensing a first paste of anode material around a first plurality of spaced-apart removable physical structures to at least partially surround each of the first plurality of spaced-apart removable physical structures with the anode material and drying the first paste;
forming a cathode layer by dispensing a second paste of cathode material around a second plurality of spaced-apart removable physical structures to at least partially surround each of the second plurality of spaced-apart removable physical structures with the cathode material and drying the second paste;
positioning an electrolyte layer in a multi-layer stack between the cathode layer and the anode layer, wherein an active cell portion of the multi-layer stack is formed by the anode layer in opposing relation to the cathode layer with the electrolyte layer therebetween;
laminating the multi-layer stack;
pulling the first and second plurality of removable physical structures out of the laminated multi-layer stack to reveal spaced-apart active passages formed through each of the anode layer and the cathode layer; and
sintering the laminated multi-layer stack to form an active cell comprising the spaced apart active passages embedded in and supported by the sintered anode material and sintered cathode material,
wherein forming one or both of the anode layer and cathode layer includes dispensing the first or second paste with a varying composition in the length direction of the removable physical structures.

6. The method of claim 5 wherein the varying composition includes alternating length portions of anode or cathode material and ceramic material for creation of a series fuel cell travelling in the length direction.

7. A method of making a monolithic fuel cell device, comprising:
forming an anode layer by dispensing a first paste of anode material around a first plurality of spaced-apart removable physical structures to at least partially surround each of the first plurality of spaced-apart removable physical structures with the anode material and drying the first paste;

forming a cathode layer by dispensing a second paste of cathode material around a second plurality of spaced-apart removable physical structures to at least partially surround each of the second plurality of spaced-apart removable physical structures with the cathode material and drying the second paste;

positioning an electrolyte layer in a multi-layer stack between the cathode layer and the anode layer, wherein an active cell portion of the multi-layer stack is formed by the anode layer in opposing relation to the cathode layer with the electrolyte layer therebetween;

laminating the multi-layer stack;

pulling the first and second plurality of removable physical structures out of the laminated multi-layer stack to reveal spaced-apart active passages formed through each of the anode layer and the cathode layer; and sintering the laminated multi-layer stack to form an active cell comprising the spaced apart active passages embedded in and supported by the sintered anode material and sintered cathode material, further comprising forming a ceramic support layer over the active cell portion and providing exposed conductive portions extending through the ceramic support layer, and repeating the steps of forming the anode and cathode layers and positioning the electrolyte therebetween to vertically stack additional active cell portions with the anode layer of one active cell portion adjacent the cathode layer of the next vertically adjacent active cell portion, with the ceramic support layer between the vertically adjacent active cell portions with the exposed conductive portion electrically connecting the active cell portions in series.

8. The method of claim 7, wherein the exposed conductive portions are formed by providing spaced via holes through the ceramic support layer and filing the via holes with conductive material.

9. The method of claim 7, wherein the exposed conductive portions are formed by providing two ceramic support layers having spaced via holes formed therein and coating one side of each of the two ceramic support layers with a conductive material and placing the coated sides in contact with each other with the via holes of one ceramic support layer offset from the via holes of the other ceramic support layer.

10. A method of making a monolithic fuel cell device, comprising:

forming an anode layer by dispensing a first paste of anode material around a first plurality of removable physical structures to at least partially surround each of the first plurality of removable physical structures with the anode material and drying the first paste;

forming a cathode layer by dispensing a second paste of cathode material around a second plurality of removable physical structures to at least partially surround each of the second plurality of removable physical structures with the cathode material and drying the second paste, wherein the each of the first and second plurality of removable physical structures have an elongate length and are positioned in the respective anode and cathode layer in parallel in the length direction and physically spaced apart from each other in a direction transverse to the length direction;

positioning an electrolyte layer in a multi-layer stack between the cathode layer and the anode layer, wherein an active cell portion of the multi-layer stack is formed by the anode layer in opposing relation to the cathode layer with the electrolyte layer therebetween;

dispensing a third paste of ceramic material around the first and second plurality of removable physical structures adjacent to the anode and cathode materials to surround each of the first and second plurality of removable physical structures with the ceramic material and drying the third paste to form a passive support portion adjacent the active cell portion in the multi-layer stack;

laminating the multi-layer stack;

pulling the first and second plurality of removable physical structures out of the laminated multi-layer stack to reveal spaced-apart passages formed in the passive support portion and transitioning through each of the anode layer and the cathode layer in the active cell portion; and sintering the laminated multi-layer stack to form an active cell with an adjacent ceramic passive support structure with the spaced-apart passages embedded in and supported by the sintered ceramic material, anode material and cathode material.

11. The method of claim 10, wherein the removable physical structures of the first and/or second plurality are straight in the length direction within the active cell portion and are curved for at least a portion of the passive support portion to exit the passive support portion of the multi-layer stack in a direction transverse to the length direction.

12. The method of claim 10, wherein the third paste is dispensed around the first and second plurality of removable physical structures adjacent each of the opposing length-wise sides of the active cell portion to form first and second passive support portions lengthwise before and after the active cell portion, respectively, whereby the spaced-apart passages in each of the anode layer and cathode layer formed after the sintering are coupled to an inlet in a first passive support structure, extend through the active cell, and are coupled to an outlet in a second passive support structure.

13. The method of claim 12, wherein the removable physical structures of the first plurality are straight in the length direction within the active cell portion and the first passive support portion, and are curved for at least a portion of the second passive support portion to form the outlet for the anode layer in the second passive support structure in a direction transverse to the length direction; and wherein the removable physical structures of the second plurality are straight in the length direction within the active cell portion and the second passive support portion, and are curved for at least a portion of the first passive support portion to form the outlet for the cathode layer in the first passive support portion in a direction transverse to the length direction.

14. The method of claim 12 wherein the first and/or second plurality of removable physical structures are curved between the inlet and outlet.

15. The method of claim 10, wherein the third paste is dispensed around the first and second plurality of removable physical structures adjacent each of the opposing length-wise sides of the active cell portion to form first and second passive support portions lengthwise before and after the active cell portion, respectively, and wherein the anode layer and the cathode layer include at least first and second sub-layers, where a first portion of the respective first or second plurality of removable physical structures extend within the first or second passive support portion and the first sub-layer and a second portion of the respective first or second plurality of removable physical structures extend within the other of the first or second passive support portion and the second sub-layer, whereby the spaced-apart passages in each of the first sub-layers of the anode layer and cathode layer formed after the sintering are coupled to an inlet in one of a first or second passive support structure and extend through the active cell, and the spaced-apart passages in each of the second sublayers of the anode layer and cathode layer formed after the sintering extend from the active cell to an outlet in the other of a first or second passive support structure.

16. The method of claim 15, wherein the second portions of the first and second plurality of removable physical structures are curved for at least a portion of the length extending within the first or second passive support portion to form the outlet in a direction transverse to the length direction.

* * * * *

UNITED STATES PATENT AND TRADEMARK OFFICE
CERTIFICATE OF CORRECTION

PATENT NO. : 9,023,555 B2  
APPLICATION NO. : 13/773044  
DATED : May 5, 2015  
INVENTOR(S) : Alan Devoe et al.

It is certified that error appears in the above-identified patent and that said Letters Patent is hereby corrected as shown below:

In the Specification

In Col. 5, line 57, "in the above-reference" should read --in the above-referenced--.

In Col. 10, lines 27-28, "portions 11$a$1 and 11$a$2 are formed" should read --portions 11$a$1 and 11$a$2 is formed--.

In the Claims

In Col. 15, line 36, Claim 8, "and filing the via holes" should read --and filling the via holes--.

In Col. 15, line 57, Claim 10, "wherein the each of" should read --wherein each of--.

In Col. 15, lines 58-59, Claim 10, "structures have an elongate length and are positioned" should read --structures has an elongate length and is positioned--.

Signed and Sealed this  
Twenty-ninth Day of September, 2015

Michelle K. Lee  
*Director of the United States Patent and Trademark Office*